United States Patent [19]

Liu

[11] Patent Number: 5,098,710
[45] Date of Patent: Mar. 24, 1992

[54] PRODUCTION OF KUGUASU

[76] Inventor: Yaguang Liu, 67-08 168th St., Flushing, N.Y. 11365

[21] Appl. No.: 606,194

[22] Filed: Oct. 31, 1990

Related U.S. Application Data

[60] Division of Ser. No. 394,558, Aug. 16, 1989, Pat. No. 4,985,248, which is a continuation of Ser. No. 63,978, Jun. 18, 1987, abandoned.

[51] Int. Cl.$^5$ .............................................. A61K 35/78
[52] U.S. Cl. .................................. 424/195.1; 514/866
[58] Field of Search ...................... 424/195.1; 514/866

[56] References Cited

PUBLICATIONS

Chem. Abstr. 96:136409e, 1982.

*Primary Examiner*—John W. Rollins
*Attorney, Agent, or Firm*—Chenpatents

[57] ABSTRACT

A new pharmaceutical composition and processes are provided for treating and preventing diabetes.

The pharmaceutical composition is composed of three ingredients: Oleanolic acid, Saponins of Litchi and Kuguasu.

The pharmaceutical composition is nontoxic.

2 Claims, No Drawings

PRODUCTION OF KUGUASU

This application is a division of application Ser. No. 07/394,558, filed Aug. 16, 1989, now U.S. Pat. No. 4,985,248, which is a continuation of application Ser. No. 07/063,978, filed Jun. 18, 1987, abandoned.

BACKGROUND OF THE INVENTION

This invention relates in general to the treatment of diabetes. More particularly, it relates to the method of reducing blood glucose and repairing disorderly metabolism in the treatment of diabetes by administering an effective amount of a pharmaceutical composition.

DESCRIPTION OF THE PRIOR ART

The major characteristic of diabetes is the body's inability to regulate the level of glucose in the blood. Therefore, the goal of treating diabetes is the reduction the blood glucose. In clinic, insulin and some oral hypoglycemic drugs, which include tolbutamide, tolazamide, acetohexamide, chlorpropamide, glyburide and glipizide, are available for treating diabetes. However, all mentioned above drugs have several disadvantages in therapeutic use. For example, some drugs are increase the risk of acute cardiovascular disease. All drugs are not effective in treating the following symptoms: diabetic acidosis or in stressful situations such as infection and the degenerative diseases which cause by diabetes. More particularly, as mentioned earlier drugs are not effective in treating atherosclerosis, lose of sight, maimed and death brought about by progressive vascular injury, and in fact, above disease is main lethal reason of diabetes.

Additionally, it has been established in the prior art that oleanolic acid can inhibited carrageenin-induced swelling in rats and inhibited capillary permeability in mice. Oleanolic acid also is used in the field of cosmetics.

SUMMARY OF THE INVENTION

It is an object of the present invention to provide a pharmaceutical composition which is safe and highly effective in treating and preventing diabetes disease.

In keeping with these objects and other objects which will become apparent hereinafter, the present invention resides, briefly stated in composition comprising a mixture of the following active ingredients:

1. Oleanolic acid extracted from fruit of *Dlospyros kaki* L. F.;
2. Saponins of Litchi extracted from fruit or seed of Litchi chinensis Sonn;
3. Kuguasu extracted from fruit of *Momordica charantia* L.

Above plants are fruit or vegetable which come into the fruit or vegetable market of U.S.

For the sake of convenience, composition comprising mixtures of the above extracts will hereinafter be referred to as "Composition".

DETAILED DESCRIPTION

According to the present invention, it has been found that pharmaceutical compositions of these ingredients have a significant blood glucose reducing effect and repairing disorderly metabolism at same time and to their use as medicine, particularly in the therapy of diabetes.

Diabetes is a disease that affects at least five percent of the America population. It is the third leading cause of death in the United States. The annual incidence of diabetes is 612,000. The economic impact of diabetes is enormous, estimated at 8 billion dollars one year. Nearly 10 percent of working persons age 45 or older are diabetics. [Entmacher, P. S. (1983): in Diabetes mellitus, theory and practise, Edited by M, Ellenbeng and H, Rifkin, pp. 1053-1061. Medical Examination Publishing Co., New York.] It is the most common serious metabolic disorder.

Diabetes is a state of absolute or relative lack of functional insulin. It is not a single disease in the classic snese; but rather a clinical syndrome applied to a number of Pathogenetically heterogenous disorders. To be exact, Diabetes is disease characterized by abnormalities of the endocrine secretions of the pancreas resulting in disordered metabolism of carbohydrate, fat and protein, and in time, structural and functional abnormalities in a variety of tissues. It also has been established in the prior art that metabolism of carbohydrate, fat, protein and hormones, et al are regulated by liver. The liver plays a key role in regulation metabolism of carbohydrate (including glucose) and is important in many other bodily functions. It manufactures blood coagulants, stores vitamins and minerals, produces enzymes, cholesterol, proteins and neutralizes substances that would harm the body. The liver can construct the storage form of many energy sources, for example, glycogen and fats. The liver can also convert glucose to protein and fat, protein into glucose, and fat into protein or glucose. Obviously, the liver plays a key role in reglation metabolism of diabetes.

For reason given above, "composition" which can reduce blood glucose and repair disordered metabolism including increasing sythesis of RNA and protein in injured liver at same time, it is very important for treating and preventing biabetes.

In addition, the composition is very safe because all plants are fruit or vegetable.

Composition can be administered to patients in the form of capsules containing a powdered mixture of the active ingredients in appropriate proportions. Alternatively, tablets can be prepared comprising the active ingredients and pharmaceutically acceptable binders, excipients, lubricants, sweeteners and coatings. A syrup or elixir may be prepared by dissolving the composition in alcohol or water together with suitable preservatives, sweeteners, dyes and flavoring agents. Ampules or vials for injection may likewise be prepared, with the composition as prepared for oral administration being purified through further sterilization and the addition thereto of distilled water and other suitable solvents and additive known in the pharmaceutical art.

The composition dosage units prepared according to the invention can be administered to patients with a very safe and in reducing blood glucose and repairing disorderly metabolism.

Oleanolic acid has the following structural formula:

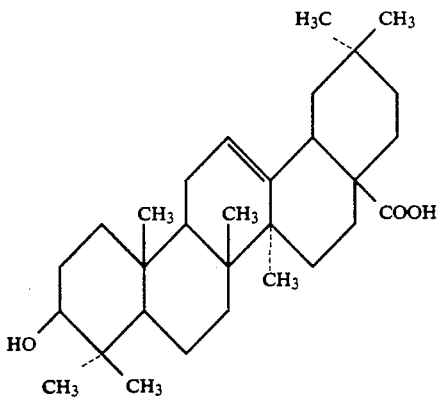

The following specific examples will provide detailed illustrations of methods of producing composition according to the present invention and pharmaceutical dosage units containing composition. Moreover, examples will be given of pharmaceutical testing performed with composition which demonstretes its effectiveness in treating and preventing diabetes. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Oleanolic Acid

Oleanolic acid extracted from fruits or leaves of *Diospyros kaki* L.F., or *Ligustrum lucidum* Ait. The fruits or leaves of *Diospyros kaki* L.F.; or *Ligustrum lucidum* Ait dried and powdered. 3 litre of 90% ethanol was added to 1 kg of dried powder and allowed to stand for one day at room temperature and then refluxed in a water bath for 6 hours. The refluxing was repeated twice by collecting the ethanol, replacing it with an equal volume of fresh 90% ethanol and refluxing for 6 hours. The refluxed ethanol was cooled and filtered and the filtrate combined with the extract filtrate. Then recovered by reduce pressure distillation and the residue dissolved in hot water. Solution of water was filtered and the filter cake (1) saved. The filter cake (1) dissolved in 95% ethanol and then PH adjusted to 11 with 1N NaOH. Solution of 95% ethanol allowed to stand and filtered. Then PH adjusted to 1 with 1N HCl. Stand. Filtered and the filter cake (2) saved. PH 11 solution of water was added to filter cake (2) and then the solution was heated to boil. Filtered. filter cake (3) saved. The filter cake (3) washed twice with water and then dissolved in ethanol and then PH adjusted to 1 with 1N HCl. Needles crystals are obtained. Wash with water. A melting point is about 310° C.

EXAMPLE 2

Extraction of Saponins of Litchi

Saponins of Litchi extracted from fruit or seed of *Litchi chinensis* Sonn. The seed or fruit of *Litchi chinensis* Sonn dried and powdered. 2,000 ml of 95% ethanol was added to 1,000 g of dried powder and allowed to stand for one day at room temperature. The solution was filtered and the extract filtrate saved. 2000 ml of ethanol was added to the residue and refluxed in a water bath for 6 hours. The refluxing was repeated twice by collecting the ethanol, replacing it with an equal volume of fresh 95% ethanol and refluxing for 6 hours. The refluxed ethanol was cooled and filtered and the filtrate combined with the extract filtrate. Ethanol was then recovered by reduced pressure distillation and the residue dissolved in 500 ml of distilled water. The lipid component was removed with 3 changes of ether by adding 500 ml to the water phase for each extraction. An equal volume of water-saturated butanol was added to the final water phase and the butanol was then distilled under reduced pressure. The residue powder was dissolved in 500 ml of ethanol and 2,000 ml of acetone was added to the ethanol with constant stirring while a precipitate formed. The precipitate was washed twice each with acetone and ether and dried.

EXAMPLE 3

Production of Kuguasu

The fruits of *Momordica charantial* L. are dried and powdered. Five liters of 90% of ethanol are added to 1 kilogram of the powder to extract Kuguasu therefrom. The ethanol mixture is adjusted to pH 2.5 by addition of hydrochloric acid. The ethanol mixture is stirred and centrifuged to recover a clear extract. A 50% zinc chloride solution, $ZnCl_2$, is added to the extract and the extract is adjusted to pH 6.8 by addition of ammonium hydroxide, $NH_4OH$. A precipitate of Kuguasu is formed and separated by centrifuging. This precipitate is dissolved in an acidic aqueous solution. NaCl solution is added to the acidic solution to form a second precipitate of Kuguasu, which is washed with acetone, dried under vacuum, and powdered.

EXAMPLE 4

Preparation of Fine Composition

Fine composition according to the present invention consists of:

|                    | Weight Percent |
|--------------------|----------------|
| Oleanolic acid     | 5 to 30%       |
| Saponins of Litchi | 10 to 50%      |
| Kuguasu            | 30 to 90%      |

The dry ingredients or derivate of ingredients prepared in accordance with the present invention, may be incorporated tablets, capsules, surups or other form by conventional method.

The tablets can be prepared by mixing the composition with binders, excipients, disintegration agents, lubricants and sweetness. Examples of widely used, pharmaceutically acceptable tablet ingredients are corn starch or gelatin as binders, dicalcium phosphate as an excipients, corn starch, potato starch or alginic acid and disintegration agents, magnesium stearate as a lubricant, and sucrose or lactose as sweetening agents. The tablets may be coated with shellac or sugar to facilitate swallowing. The preferred weight ranges of the composition in tablets are the same as given above for capsule dosage forms. The most preferred weight values for the components are, as in the case of capsules, 50–100 mg of dry ingredients per dosage unit.

Elixirs or syrups may be prepared by dissolving composition in water or ethanol and, if desired, adding a sweetener such as sucrose, a suitable preservative, a dye (chosen according to the desired coloration) and a flavoring agent, such as an orange or cherry flavor. The concentration ranges of the composition per teaspoon (5 milliliters) of syrup are the same as given above for capsule and tablet dosage units.

EXAMPLE 5

Preparation of Crude Composition

Crude composition is extracted from as mentioned above plants by ethanol and water. Proportion of plants, for example, is as following (by weight):

|  | Weight Percent |
|---|---|
| Diospyros kaki L.F., | 5 to 50% |
| Litchi chinesis Sonn | 10 to 70% |
| Momordica charantia L. | 10 to 70% |

The tissues of plants were dried and powdered. 5 liters distilled water was added 1 kg of dried powder. The solution was heated to boil and simmered for one hour after boiling. This water extraction was repeated two times. Combined and filtered. The filtrate was concentrated under reduced pressure to approximately 500 ml. Then 2,000 ml of 90% ethanol was added to 500 ml water solution. Stir. Stilled. Filtered. Residue and filtrat (A) was obtained. 1,000 ml 90% ethanol was added to residue. Stir. Stilled. Filtered. filtrate (B) was obtained.

Combined filtrate (A) with (B). Then total filtrate was concentrated to syrup under reduced pressure distillation. Ethanol was recoved. Syrup dried under vacuum drying. Granulated to final powder. Weight of every capsule and table is about 200-500 mg. Crude-composition is similar to fine-composition in pharmacological property.

The following examples are related to pharmacological tests.

EXAMPLE 6

Hypoglycemic Effect of Composition

Experiments use alloxan diabetic mice. Male mice 18-22 g were used in these experiments. The diabetic mice had high blood glucose, produced by a single dose of alloxan 75 mg/kg intravenously. Inject 2 ml of normal saline into the peritoneal cavity of mouse for control and 100 mg/kg composition group daily. Blood samples were collected from ocular venous plexus of mice.

The blood glucose levels were determined according to hexokinase method. The procedure is as the following:

A. Reagents

1. Vial B, containing NADP. Reconstitute by adding 15.5 ml water and gently swirling.
2. Vial A. Add the entire contents of vial B to vial A and dissolve by gently inversion. According to the manufacturer, the reagent has the following composition:
   a. Tris buffer, pH 7.5, 50 mmol/L
   b. ATP, 0.5 mmol/L
   c. NADP+, 0.45 mmol/L
   d. Mg++, 17 mmol/L
   e. Hexokinase, 666 U/L
   f. G6PD, 333 U/L
3. Stock Standard Glucose, 10.0 g/L. Dissolve 1.0 g pure anhydrous D-glucose in water containing 1.0 g benzoic acid per liter. Make up to 100 ml volume in the benzoic acid solution.
4. Working Glucose Standards. Prepare standards of 50, 100, 200, and 400 mg/dl by appropriate dilution of Stock Standard with benzoic acid solution.

B. Procedure

1. Place 1.5 ml prepared reagent in a series of cuvets for standard, unknowns, and control serum, respectively.
2. Appropriate blanks are set up by placing 1.5 ml of 9 g/L NaCl in a series of cuvets.
3. Add 10 μl of standard, unknowns and control serum to the appropriate cuvets [tests and blanks]. Cover with Parafilm and mix. Place in 37° C. incubator for a faster reaction. It is permissible to carry out the reaction at room temperature, even though it takes longer for the reaction to go to completion.
4. After incubating for 5 or 10 minutes, read the absorbance of each cuvet at 340 nm and check again a few minutes later to insure that an end point has been reached.
5. Calculation. Let $\Delta A$ be the difference in absorbance reading between each test and its blank.

$$\text{Glucose concentration (mg/dl)} = \frac{\Delta A_u}{\Delta A_s} \times C$$

Where C=concentration of standard in mg/dl, $\Delta A_u$ and $\Delta A_s$ are the respective difference in absorbance between unknown or standard and its blank.

TABLE 1

|  | Control | Composition |
|---|---|---|
| Blood glucose level (mg/dl) | 245.3 ± 36.6 | 171.5 ± 18.9 |
| Number of samples | 20 | 20 |
| P |  | <0.1 |

From above results, it is apparent that composition can obviously decrease blood glucose levles in diabetic model.

EXAMPLE 7

Effect of Composition on Binding Insulin Receptor

Rats were sacrificed by a blow on the head, and their epididymal adipose tissue were quickly removed. The fat cell were isolated from the adipose by the procedure of Rodbell (Rodbell, M.: J. Biol Chem, 239:375, 1964). In dulbecco buffer PH 7.4 containing collagenase (3 mg/ml) and albumin (40 mg/ml).

$^{125}$I-labeled insulin ($^{125}$I-insulin) was at specific activities of 100-200 μCi/μg. IgG was prepared from heparinized plasma. The IgG fraction of serum from the patient with the highest concentration of antireceptor antibody activity (B-2) was prepared from the ammonium sulfate precipitate by ion exchange chromatography of DEAE-cellulose. Antireceptor antibodies were assayed by methods of inhibition of $^{125}$I-insulin binding to cultured human lymphoblostoid cells. The cells were prepared: 2-4×10$^6$ cells/ml of adipocytes cells were washed three times for 10 minutes at 37° C. and nondissociable radioactivity was extracted in 1% triton X-100. $^{125}$I-insulin binding to isolated rat adiposytes were performed at 37° C. in krebs-ringer bicarbonate medium (PH 7.4) containing bovine serum albumin and bacitracin (100 U per milliliter). After adipocytes had been incubated with $^{125}$I-insulin for 30 minutes at 37° C., the cell were precipitated from the medium by centrifugation. The radioactivity in the pellet was counted.

TABLE 2

|  | Control | Composition |
| --- | --- | --- |
| The binding of $^{125}$I-insulin receptor | 100% | 120.0 ± 14.0% |
| The number of samples | 10 | 10 |
| P |  | <0.05 |

From above results, it is apparent that composition can obviously stimulate binding insulin receptor with insulin.

EXAMPLE 8

The Effect of Composition on Synthesis of Protein

The 20–22 g male mice were used in experiments. The mice were injected with CCl$_4$. The dosage of composition was 75 mg/kg injected intraperitoneally. the control mice were injected with same volume of normal saline. The mice were sacrificed by decapitation. their liver was quickly excised and placed immediately in cold Medium which consisting of 0.25M sucrose, 0.065M potassium chloride, 0.035M potassium bicarbonate, 0.01M magnesium chloride and 0.05M tris (hydroxymethyl) aminomethane (Tris), adjusted to pH to 7.5 with HCl. The liver was cleaned of excess fat before the wet weight was measured. The liver from each animal were homogenized in each experiment. All operations were performed at 4° C. Each liver was homogenized in 10 ml of cold Medium, Using a Teflon and glass homogenizer immersed in ice. The homogenate was centrifuged at 1000 g for 10 minutes to remove large cellular particles. the resulting supernatant fluid was filtered through four layers of cloth to remove as much fatty material as possible. The filtrate was centrifuged at 37,000 g for 30 minutes. The sediment was discarded, and the resulting postmitochondrial fraction was used for the assay of translation. Protein concentration was measured by the biuret procedure [J. Biol Chem 177:751, 1949], using crystalline bovine serum albumin as a standard. The rate of translation was determined in an assay system containing: 0.2 ml of 0.01M ATP, 0.2 ml of 0.05M phospho puruvate, 0.05 ml of a $^3$H-amino acid mixture (containing approximately 5×10$^6$ cpm), 0.05 ml of crystalline pysuvate kinase (1 mg/ml), 0.1 ml of water and 1.0 ml of the postmitochondrial preparation in Medium in a total volume of 2 ml. The postmitochondrial preparation was added last to initiate the reaction, and the mixture was incubated for 30 minutes at 37° C. Under the conditions of the experiment, translation was a straight-line function of time for at least 45 minutes. The course of the reaction was halted by the addition of 5 ml of 10% trichloroacetic acid (TCA). Control tubes were prepared by adding all of the components of the reaction mixture into 5 ml of 10% TCA. The precipitated proteins were collected on a 0.45-μm membrane filter, using vacuum filtration. The collected precipitate was washed two times with 20 ml portions of 10% TCA and dried in an oven at 80° C. for 10 minutes. The dried filters were placed in scintillation vials containing 20 ml of Aquasol, and the radioactivity which had been incorporated into protein was measured in a liquid scintillation counter.

|  | Control | Composition |
| --- | --- | --- |
| CPM/mg Proteins | 639 ± 81 | 891 ± 88 |
| Number of sample | 18 | 18 |

-continued

|  | Control | Composition |
| --- | --- | --- |
| P |  | <0.01 |

EXAMPLE 9

The Effects of Composition on Ribonucleic Acid (RNA)

The method of animal is like procedure of example 8. $^3$H-uridine (10 μCi/100 g body weight) was injected intraperitoneally into mice 20 minutes prior to sacrifice. Their liver was quickly excised. Livers were washed with cold 0.25M sucrose containing 3.3 mM CaCl$_2$ and minced with scissors. The mince was then homogenized with 3 volumes of the same solution in a Potter's homogenizer with a glass pestle and centrifuged at 1000×g for 10 minutes. the sediment was homogenized with 3 volumes of 0.25M sucrose-3.3 mM CaCl$_2$ in a Potter's homogenizer with a Teflon pestle. The homogenates were filtered through 4 layers of gauze. Eight volumes of 2.2M sucrose was added and the mixture was centrifuged at 40000×g for 1 hour to sediment the nuclei. Purified nuclei were washed with 0.6N perchloric acid, ethanol and ether. To the residues was added 0.5N KOH and the mixture was incubated at 37° C. for 18 hours, followed by acidification to remove deoxyribonucleic acid (DNA) and proteins as precipitates. After centrifugation the supernatant was neutralized with KOH. Radioactivity incorporated into nuclear RNA and the amount of RNA were determined using aliquotes of this supernatant. Radioactivity was counted in a scintillation spectrometer with solution, the composition of which was as follows: one liter of the solution contained 50 ml of methanol, 10 ml of ethyleneglycol, 60 g of naphthalene, 4 g of 2,5-diphenyloxazole, 0.2 g of 1,4-bis[2(5phenyloxaxolyl)]-benzene and dioxane.

TABLE 4

|  | Control | Composition |
| --- | --- | --- |
| Specific radioactivity (CPM/mg RNA) | 18090 ± 1819 (n = 18) | 21888 ± 2079 (n = 18) |
| P |  | <0.01 | n: the number of samples

EXAMPLE 10

Safety of Composition

1. The acute LD$_{50}$ of fine composition was found to be 1469 mg/kg injection in abodominal cavity in mice.

2. L.D$_{50}$ of crude-Composition: 5.4 g/kg injection in abodominal cavity in mice.

3. Each dose for an adult is 500–1000 mg. Using 50 kg as the average weihgt of an adult the dosage is 1–10 mg/kg, therefore, it is very safe.

4. As to subacute toxicity tests, a dosage corresponding to 50 times the clinical dose is administered continually for two months, and no side-effects have been observed. The electrocardiograms and functions of liver and the kidney have not been affected and no injuries whatever have been observed in the tissue slices of the heart, liver, spleen, lungs, kidneys and adrenal.

The preparation of composition is simple and can be accomplished by the extraction methods set forth above or any conventional methods for extracting the active ingredients. The novelty of the present invention resides in the mixture of the active ingredients in the specified proportions at invention and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, tablets, capsales, syrups, elixirs, and solutions for parenteral injection with specified ranges of composition.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by letters patent is set forth in the appended claims.

1. A process 8 or producing Kuguasu comprising:
   a. extracting dried and powdered fruits of *Momordica charantia* L with 90% ethanol;
   b. adjusting the ethanol mixture to pH 2.5 with hydrochloric acid;
   c. separating the ethanol extract from the powdered residue;
   d. adding 50% zinc chloride solution to the ethanol extract and precipitating crude Kuguasu by neutralizing the ethanol solution to pH 6.8 with ammounium hydroxide; and
   e. recovering the crude Kuguasu.

2. The process of claim 1 further comprising: dissolving the crude Kugusa in an acidic solution; precipitating the product Kuguasu with addition of sodium chloride; recovering Kuguasu, washing the same with acetone and drying the same under vacuum.

* * * * *